United States Patent [19]

Taylor

[11] 4,259,960
[45] Apr. 7, 1981

[54] CATHETER WITH NON-ADHERING BALLOON

[75] Inventor: Glenn N. Taylor, Cary, Ill.

[73] Assignee: The Kendall Company, Boston, Mass.

[21] Appl. No.: 85,177

[22] Filed: Oct. 15, 1979

Related U.S. Application Data

[63] Continuation of Ser. No. 846,291, Oct. 28, 1977, abandoned.

[51] Int. Cl.³ ............................................ A61M 25/00
[52] U.S. Cl. ................................................ 128/349 B
[58] Field of Search .............................. 128/348–350, 128/325, 344, 246, 207.15; 264/242, 264

[56] References Cited

U.S. PATENT DOCUMENTS

| | | | |
|---|---|---|---|
| 2,248,934 | 7/1941 | Auzin | 264/264 |
| 2,330,400 | 9/1943 | Winder | 264/264 |
| 3,452,756 | 7/1969 | Harautuneian | 128/349 B |
| 3,467,101 | 9/1969 | Fogarty et al. | 128/348 |
| 3,539,674 | 11/1970 | Dereniuk et al. | 264/264 X |
| 3,585,983 | 6/1971 | Kantrowitz et al. | 128/344 X |
| 3,924,634 | 12/1975 | Taylor et al. | 128/349 B |

Primary Examiner—Dalton L. Truluck
Attorney, Agent, or Firm—Powell L. Sprunger

[57] ABSTRACT

A catheter comprising, an elongated shaft having a main lumen, an inflation lumen extending along the shaft, and an outer surface. The catheter has an annular sleeve of elastic material joined to the shaft in spaced first and second circumferential zones defining a cavity intermediate the sleeve and shaft. The inflation lumen communicates with the cavity to inflate the sleeve, and the sleeve has an inner surface facing toward the outer surface of the shaft. The inner surface of the sleeve is separated from the outer surface of the shaft in spaced areas intermediate the first and second zones, with the sleeve being permitted to contact the shaft in regions intermediate the areas.

4 Claims, 7 Drawing Figures

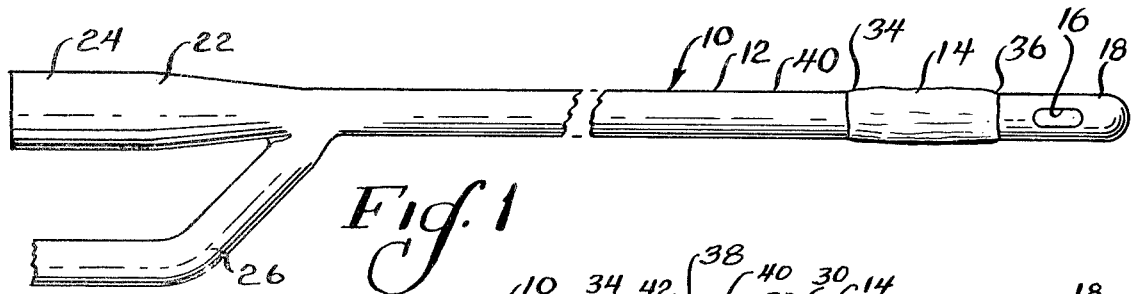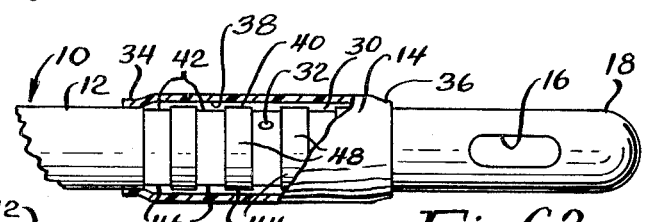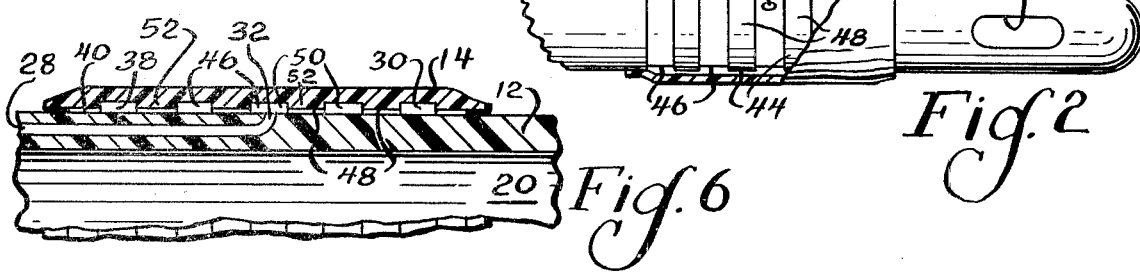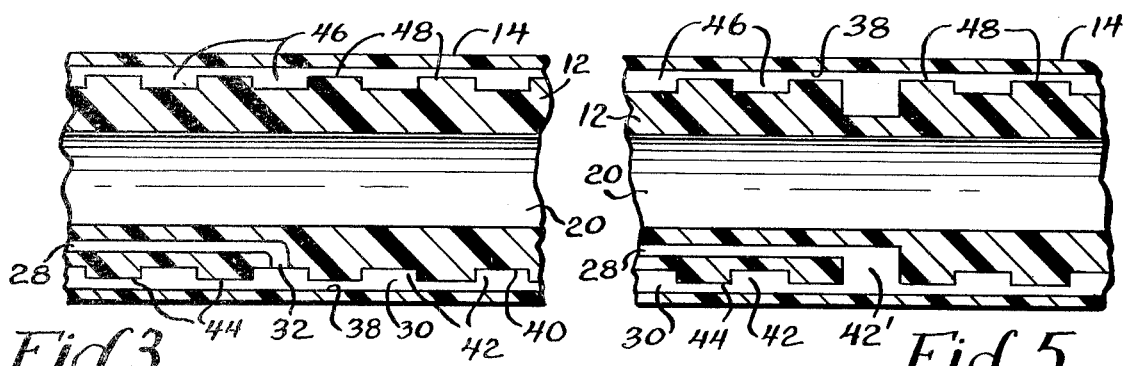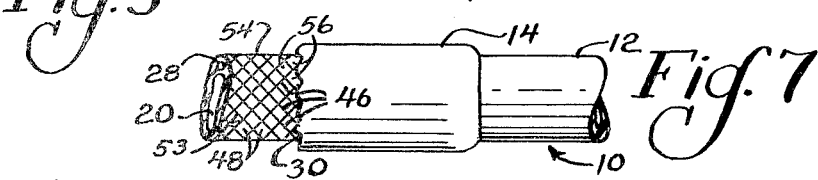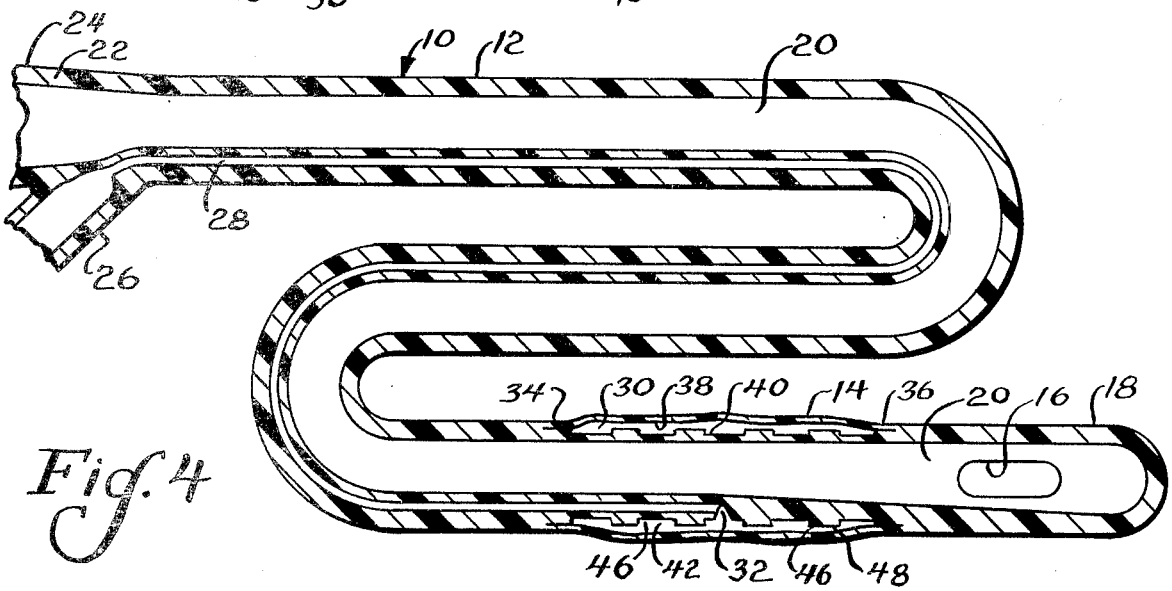

CATHETER WITH NON-ADHERING BALLOON

This is a continuation, of application Ser. No. 846,291 filed Oct. 28, 1977 now abandoned.

BACKGROUND OF THE INVENTION

The present invention relates to catheters.

A various assortment of catheters, such as Foley catheters and endotracheal tubes, have been proposed for use on patients. In the case of Foley catheters, a distal end of the catheter is passed through the urethra in the patient until an inflatable balloon located adjacent the distal end of the catheter is positioned in the patient's bladder, and the balloon is then inflated in order to retain the catheter in place in the patient. During catheterization, urine drains from the bladder through drainage eyes adjacent the distal end of the catheter, through a drainage lumen in the catheter, and through a drainage tube connected to a proximal end of the catheter into a collection bag for retention therein.

Although such catheters are generally satisfactory for their intended use, it has been found that when certain materials are utilized for the catheter balloon and shaft, such as latex rubber or silicone, the balloon tends to adhere to the catheter shaft at the time of use, particularly in instances where there has been some delay between the date of manufacture and date of use of the catheter, e.g., 5 to 6 months. In certain cases, the entire balloon adheres to the shaft with sufficient tack to prevent inflation of the balloon. In other cases, certain areas of the balloon stick to the shaft, resulting in distortion of the balloon when it is inflated.

SUMMARY OF THE INVENTION

A principal feature of the present invention is the provision of a catheter of simplified construction having improved inflation characteristics of the catheter balloon.

The catheter of the invention comprises, an elongated shaft having a main lumen, an inflation lumen extending along the shaft, and an outer surface. The catheter has an annular sleeve of elastic material joined to the shaft in spaced first and second circumferential zones defining a cavity intermediate the sleeve and shaft, with the inflation lumen communicating with the cavity to inflate the sleeve, and with the sleeve having an inner surface facing toward the outer surface of the shaft. The catheter has means for separating the inner surface of the sleeve from the outer surface of the shaft in spaced areas intermediate the first and second zones, with the sleeve being permitted to contact the shaft in regions intermediate the areas.

A feature of the present invention is that the separating means prevents adherence of the sleeve to the shaft in the areas of separation.

Thus, another feature of the present invention is that the sleeve may be readily inflated without adherence to the shaft at the time of use.

Still another feature is that the invention thus minimizes the possibility that the catheter may be rendered inoperative due to non-inflation or distortion of the balloon at the time of use.

Further features will become more fully apparent in the following description of the embodiments of this invention and from the appended claims.

DESCRIPTION OF THE DRAWINGS

In the drawings:

FIG. 1 is a fragmentary elevational view of a catheter of the present invention;

FIG. 2 is a fragmentary elevational view, partly broken away, of the catheter of FIG. 1;

FIG. 3 is a fragmentary sectional view of the catheter of FIG. 2;

FIG. 4 is a fragmentary sectional view of the catheter of FIG. 1;

FIG. 5 is a fragmentary sectional view of another embodiment of the catheter of the present invention;

FIG. 6 is a fragmentary sectional view of another embodiment of the catheter of the present invention; and FIG. 7 is a fragmentary elevational view of another embodiment of the catheter of the present invention.

DESCRIPTION OF THE PREFERRED EMBODIMENTS

Referring now to FIGS. 1-4, there is shown a catheter generally designated 10 having an elongated shaft 12 and an inflatable balloon comprising an annular sleeve 14 of elastic material. The catheter shaft 12 and sleeve 14 may be made of any suitable material, such as silicone or latex rubber. Although, for convenience, the invention will be described in connection with a urinary or Foley catheter, it will be understood that the principals of the invention may be applied to any suitable catheter, such as an endotracheal tube.

As shown, the shaft 12 has at least one drainage eye 16 adjacent a distal end 18 of the shaft 12, and a main or drainage lumen 20 extending through the shaft. The catheter has a connector 22 at a proximal end 24 of the catheter which may be connected to a drainage tube (not shown) during catheterization. The catheter has a side arm 26 having valve means of suitable type (not shown) for use in inflating the sleeve 14. The catheter shaft 12 has an inflation lumen 28 extending through a wall of the shaft and communicating between the side arm 26 and a cavity 30 intermediate the sleeve 14 and shaft 12. Thus, the inflation lumen 28 communicates with the cavity 30 through an opening 32 in the wall of the shaft 12 to permit pumping of fluid through the side arm 26, the inflation lumen 28, and the opening 32 into the cavity 30 in order to inflate the sleeve or balloon 14.

The sleeve 14 is joined to the shaft 12 at spaced first and second circumferential zones 34 and 36, such that the zones 34 and 36 close the ends of the cavity 30. The sleeve 14 may be joined to the shaft 12 in the zones by any suitable bonding means, such as adhesive or heat sealing. In this configuration, the sleeve 14 has an inner surface 38 facing toward an outer surface 40 of the shaft 12 beneath the sleeve.

The shaft 12 has a plurality of spaced circumferential recesses 42 in the outer part of the shaft defining a plurality of spaced circumferential or annular ridges 44 intermediate the recesses 42. The recesses 42 may be formed in any suitable manner, such as by grinding material from the shaft in the area of the recesses. The shaft recesses 42 define areas 46 of separation between the inner surface 38 of the sleeve 14 and the outer surface 40 of the shaft 12 which are located intermediate the first and second circumferential bonding zones 34 and 36. The ridges 44 define a plurality of regions 48 which separate the areas 46 from each other, such that the sleeve 14 is permitted to contact the shaft 12 in the spaced regions 48 for support of the sleeve.

In accordance with the present invention, the separating areas 46 defined by the recesses 42 prevent contact of the sleeve 14 with the shaft 12 in the areas, thus reducing the total region of contact between the sleeve and shaft. In this manner, the catheter minimizes the possibility that the sleeve may adhere to the shaft at the time of use due to the nature of the sleeve and shaft materials, particularly in the case of silicone or latex rubber catheters, which otherwise might prevent inflation of the balloon or cause distortion of the balloon when inflated.

Another embodiment of the present invention is illustrated in FIG. 5, in which like reference numerals designate like parts. In this embodiment, at least one of recesses 42' extends to the depth of the inflation lumen 28 in the shaft wall, such that the recess 42' communicates directly with the inflation lumen. If desired, additional recesses in the areas 46 may extend to the depth of the inflation lumen.

Another embodiment of the present invention is illustrated in FIG. 6, in which like reference numerals designate like parts. In this embodiment, the areas 46 are defined by circumferential recesses 50 in the inner part of the sleeve 14. The recesses 50 define spaced circumferential ridges 52 in the sleeve 14 intermediate the recesses 50, such that the ridges 52 separate the areas 46 in regions 48 defined by the ridges 52. As before, the sleeve 14 and shaft 12 are separated in the areas 46 to minimize the possibility of adherence of the sleeve to the shaft at the time of use of the catheter.

Another embodiment of the present invention is illustrated in FIG. 7, in which like reference numerals designate like parts. In this embodiment, the sleeve 14 is separated from the shaft 12 in areas 46 defined by strands 53 of a scrim material or sleeve 54 which extends around the shaft in the cavity intermediate the sleeve 14 and shaft 12. The scrim sleeve 54 has a plurality of openings 56 which define the regions 48 between the sleeve and shaft, and which are separated by areas 46 defined by the strands 53. As before, the scrim sleeve 54 minimizes the possibility that the sleeve 14 may become adhered to the shaft 12 at the time of use of the catheter.

The foregoing detailed description is given for clearness of understanding only, and no unnecessary limitations should be understood therefrom, as modifications will be obvious to those skilled in the art.

I claim:
1. A catheter, comprising:
an elongated shaft having a main lumen, an inflation lumen extending along the shaft, and an outer surface;
an annular sleeve of elastic material joined to the shaft in spaced first and second circumferential zones defining a cavity intermediate said sleeve and shaft, said inflation lumen communicating with the cavity to inflate said sleeve, and said sleeve having an inner surface facing toward a region of said outer surface of the shaft underlying the sleeve, with said surface region of the shaft being substantially smooth; and
said sleeve having a plurality of inner spaced circumferential ridges having inner surfaces facing toward the outer surface region of the shaft, said ridges defining a plurality of circumferential recesses having surfaces intermediate the ridge inner surfaces, with the inner surfaces of said ridges contacting the outer surface region of the shaft until use of the catheter, and said ridges having a sufficient width relative to the width of the recesses to prevent contact of the recess surfaces with the outer surface region of the shaft when the ridge inner surfaces contact the outer surface region of the shaft.

2. The catheter of claim 1 wherein said sleeve is constructed from a silicone material.

3. The catheter of claim 1 wherein said sleeve is constructed from a latex material.

4. A catheter, comprising:
an elongated shaft having a main lumen, an inflation lumen extending along the shaft, and an outer surface;
an annular sleeve of elastic material joined to the shaft in spaced first and second circumferential zones defining a cavity intermediate said sleeve and shaft, said inflation lumen communicating with the cavity to inflate said sleeve, and said sleeve having an inner surface facing toward said outer surface of the shaft; and
means for separating the inner surface of the sleeve from the outer surface of the shaft in spaced areas intermediate said first and second zones, said sleeve being permitted to contact the shaft in regions intermediate said areas, said separating means comprising an open-mesh scrim material extending around the shaft and having a plurality of crossing strands defining a plurality of openings.

* * * * *